United States Patent [19]
Lustig

[11] Patent Number: 4,575,340
[45] Date of Patent: Mar. 11, 1986

[54] PRECISION DENTAL RESTORATIVE SYSTEM

[76] Inventor: Leopold P. Lustig, 304 Greenwood St., Newton Centre, Mass. 02159

[21] Appl. No.: 698,677
[22] Filed: Feb. 4, 1985
[51] Int. Cl.[4] .............................................. A61C 8/00
[52] U.S. Cl. .................................... 433/173; 433/221
[58] Field of Search ....................... 433/173, 176, 221

[56] References Cited
U.S. PATENT DOCUMENTS

| | | | |
|---|---|---|---|
| 622,670 | 4/1899 | Dwight | 433/221 |
| 640,551 | 1/1900 | Fones | 433/221 |
| 3,837,080 | 9/1974 | Pasqualini | 433/176 |

Primary Examiner—Robert Peshock
Attorney, Agent, or Firm—Alfred H. Rosen

[57] ABSTRACT

A prefabricated abutment of precise size, shape and dimensions is fixed in a patient's jawbone, as the supragingival part of an endodontic post, or an implant, for example. The post is used in combination with a prefabricated sleeve-like coping which is telescopically mated to the post with a high degree of dimensional precision. A finished crown is fixed rigidly to such a coping, or replicates its internal dimensions, so as to use the post as its support.

30 Claims, 22 Drawing Figures

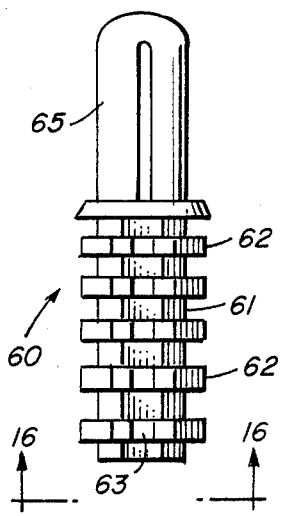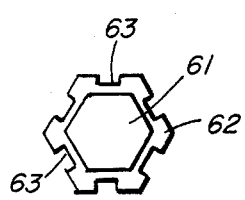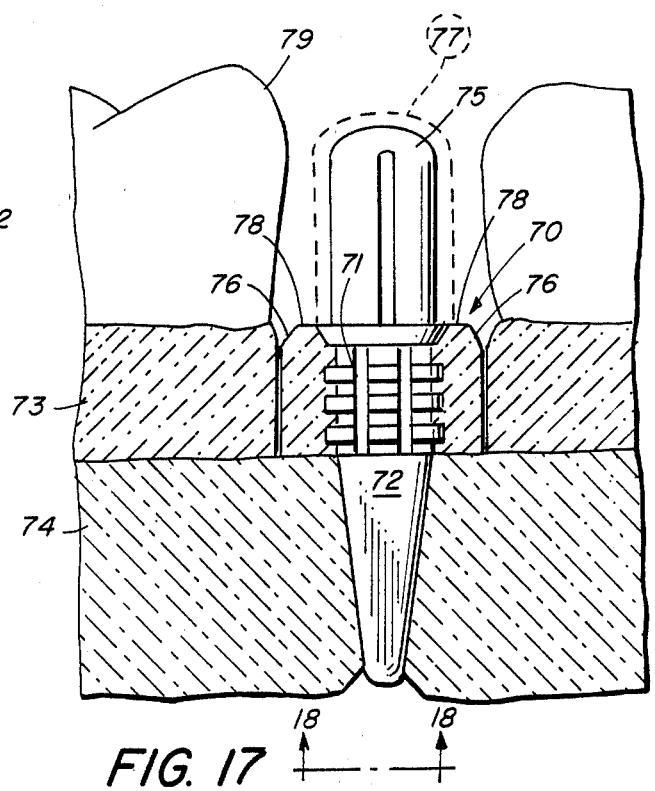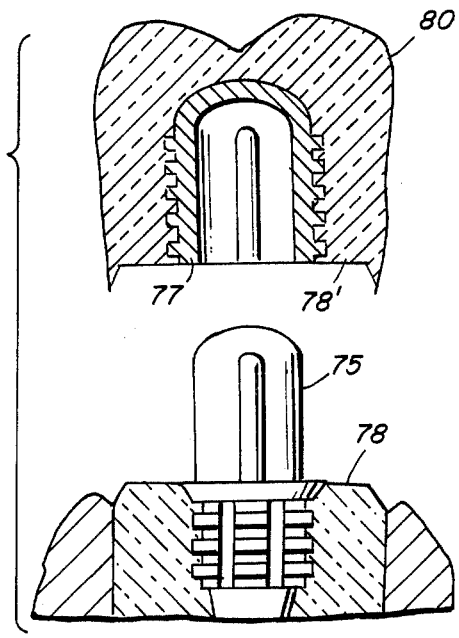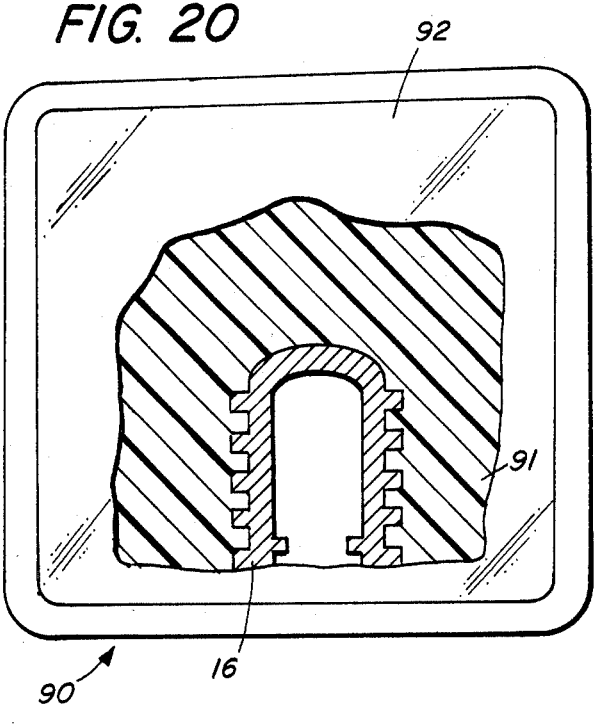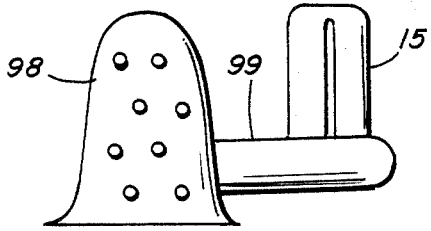

PRECISION DENTAL RESTORATIVE SYSTEM

INTRODUCTION

In the art of dentistry, it has long been recognized that crowns can be attached and supported by posts which in turn are fixed, or supported in root canals, or on implants in cases where root structures are not available. At the present state of development, however, each such post is custom fitted and formed as a unique support for a coronal reconstruction, which itself may be a single crown or a part of a bridge or splint which includes two or more crowns rigidly fixed together. This is an expensive and time-consuming procedure.

GENERAL NATURE OF THE INVENTION

This invention provides a prefabricated abutment of precise size, shape and dimensions, which is fixed in the patient's jawbone in any of a variety of ways, for supporting a single crown or a multi-tooth bridge, and new methods for fabricating abutments and crowns precisely, quickly and by less labor intensive means and procedures. Savings in labor and time, greatly enhanced accuracy, which is not obtainable by manual means, and predictable results are all made possible with the invention.

Abutments according to the invention are based on the use of a prefabricated post which is fixed in the patient's jawbone, either as the supra-gingival part of an endodontic post, or an implant, or as a cantilevered extension from an abutment crown or tooth, for example. The post is used in combination with a prefabricated sleeve-like coping which is telescopically mated to the post with a high degree of dimensional precision. A finished crown is fixed rigidly to a coping.

For laboratory procedures the invention provides dowel pins which exactly replicate the post that is fixed in the patient's mouth. Such dowel pins are provided in a variety of combustible and non-cumbustible materials suitable for laboratory procedures. In one form, the dowel pin has a supra-gingival post extending from an anchor part which is formed for retention in a rigid die material such as casting stone, or in a refractory material. In another form, the dowel pin has a supra-gingival post extending from an anchor part which is formed for retention in a rigid die material, followed by a tapered knock-out dowel, for use in shaping individual abutments, to gain proximal and gingival access. In all forms, the supra-gingival post part is a precision replication in size, shape and dimensions of the post that is fixed in the patient's mouth; it is prefabricated, and not duplicated by taking impressions. The dowel pins may be made of combustible material, or of refractory material, or metal or non-combustible plastic, as may be indicated for the specific laboratory procedure being used.

According to the invention, impressions are taken with the prefabricated coping in place on its mated post that has been fixed in the patient's jawbone. Depending on the restoration procedure to be used, the coping can be made of a combustible or a non-combustible material. The finished crown or bridge includes the coping or a precision replica of the internal dimensions of the coping, and is put in place on the patient's post, or posts, by telescopically fitting the included coping or copings over the patient's post or posts. The posts and copings are provided with means to retain the included copings on their mated posts, either permanently or removably.

According to the invention, a crown can be constructed at chairside, on a coping fitted to the post fixed in the patient's jawbone. To this end, the invention provides a prefabricated assembly of a coping and dental restorative material which can be formed and hardened after the coping has been fitted to the patient's post.

Posts and copings according to the invention are industrially made, to a high degree of precision, in a family of sizes, shapes and lengths. The posts and copings may be made to fit together non-rotationally, and if desired, locking or latching means can be included. The copings have retentive means for holding dental restorative materials and finished crowns fixed rigidly to them.

BRIEF DESCRIPTION OF THE DRAWINGS

FIG. 15 is a side view of a dowel pin according to the invention, intended for labortory use;

FIG. 16 is a bottom view of the pin in FIG. 15, taken on line 16—16;

FIG. 17 is a side view of a removable dowel pin according to the invention, shown in rigid die material, foe use to gain proximal and gingival access when shaping an individual abutment;

FIG. 18 is a partial view on line 18—18 of FIG. 17;

FIG. 19 shows a tooth reconstructed according to the invention;

FIG. 20 shows a prefabricated package containing a coping sleeve according to the invention and a dental restorative material in a mastic state; and FIG. 21 illustrates a post according to the invention supported as a cantilevered extension from an abutment coping.

DETAILED DESCRIPTION

Figure 1:
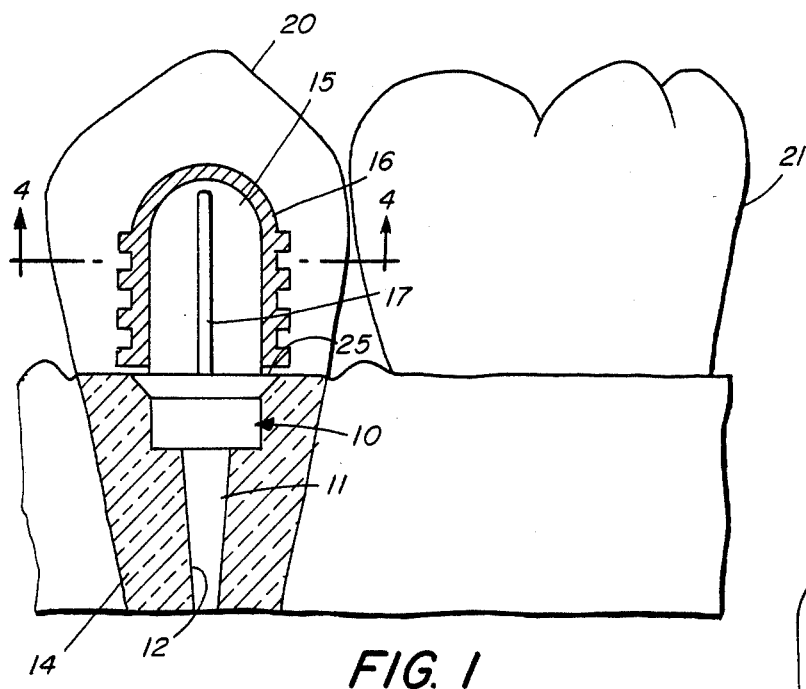
FIG. 1 illustrates an endodontic post and coping sleeve according to the invention in place in a posterior quadrant containing other teeth.
Figure 4:
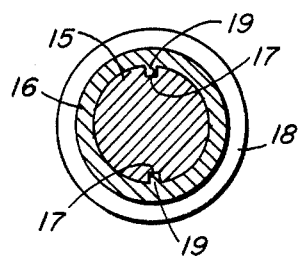
FIG. 4 is a section on line 4—4 of FIG. 1.

In FIG. 1 an endodontic post 10 is shown with its subgingival portion 11 in the root canal 12 of a tooth 14, the coronal portion of which tooth is missing. The supra-gingival part 15 of the post is encased by a coping sleeve 16 which is externally fitted with retaining means, in this instance projections 18, for rigidly holding a dental reconstruction 20 (shown in dotted line), formed on the coping sleeve. The supra-gingival post 15 has two longitudinal grooves 17 running down its sides, as shown in FIG. 4, which mate with projections 19 extending radially inward from the coping sleeve, to prevent rotation of the coping sleeve around the post.

According to the present invention, the supra-gingival post part 15 is furnished in a family of precisely established external sizes, shapes and dimensions, and the coping sleeves are likewise furnished in a corresponding family of precisely established internal sizes, shapes and dimensions, and a dental restoration is formed on a coping sleeve which is mated to the supra-gingival post 15 on which the restoration will be supported, or alternatively the restoration incorporates a faithful replica of that sleeve's internal size, shape and dimensions.

FIG. 1 shows an additional tooth 21 in the same posterior quadrant. An impression of this quadrant, for laboratory use to be duplicated for restoration purposes, will be taken with the coping sleeve 16 in place on the supra-gingival post 15, and the coping sleeve 16 will be removed with the impression. Thereafter, the coping sleeve in the impression will be used for precise location and placement of one or more laboratory dowel pins in a rigid die material, or in a refractory material, as will presently be described. Alternatively, a restoration can be fashioned on the coping sleeve 16 at chairside. The invention provides a wide range of options to restorative dentistry, ranging from same-day restoration of damaged or destroyed teeth, to restoration requiring two or more visits to the dentist but even then more precisely, more quickly and with less labor-intensive means and procedures.

Figure 2:
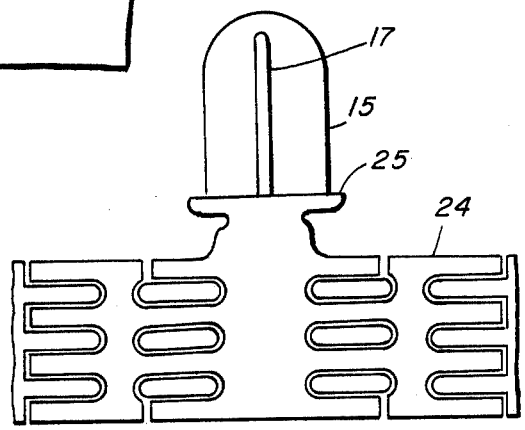
FIG. 2 shows a post according to the invention mounted on a blade implant.
Figure 3:
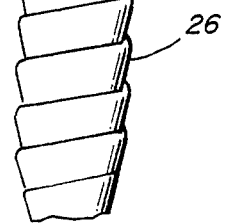
FIG. 3 shows a post according to the invention mounted on a screwtype implant (i.e.: a bone screw)

Supra-gingival posts 15 according to the invention can be applied in conjunction with dental implants, two examples of which are shown in FIGS. 2 and 3. In FIG. 2 the post 15 is affixed to blade implant 24. In FIG. 3, the post 15 is incorporated in a screw-type implant 26 in the form of a bone screw. In like manner the supra-gingival post 15 can be applied in conjunction with, or incorporated in osseointegrated implant devices, procedures and modalities. It will be understood that in all such instances the supra-gingival post 15 is supported from the patient's jawbone. Each embodiment of the supra-gingival post 15 has a bottom shoulder 25 against which the coping sleeve 16 can abut when it is installed on the post. The post can have sides that are parallel, or slightly tapered toward the free end, to facilitate installation of multiple abutments.

Figure 5:
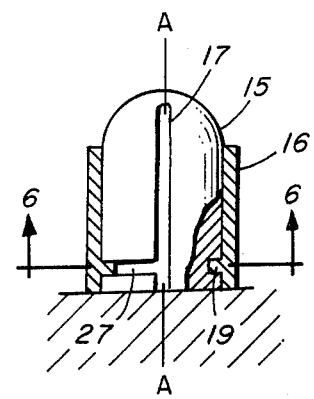
FIG. 5 illustrates a bayonet-type locking mechanism for locking a coping sleeve on a post.
Figure 6:
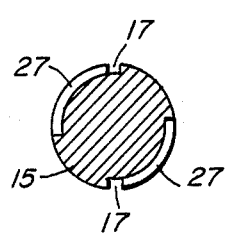
FIG. 6 is a section on line 6—6 of the post shown in FIG. 5.
Figure 7:
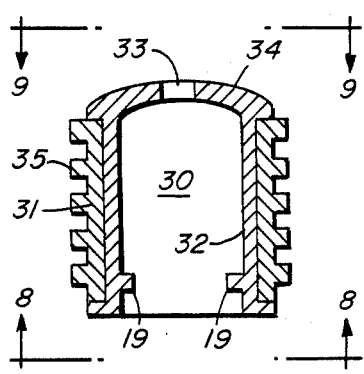
FIG. 7 is a longitudinal sectional view of a two-part coping sleeve which can be detachably locked on the post shown in FIG. 5.
Figure 9:
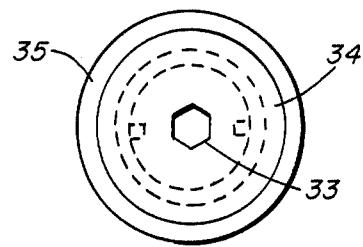
FIG. 9 is a view from line 9—9 of FIG. 7.
Figure 8:
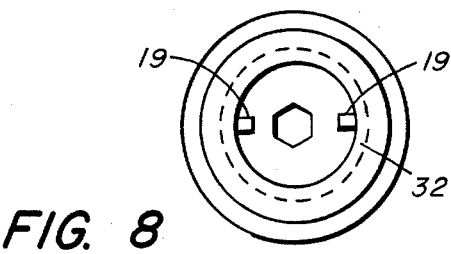
FIG. 8 is a view from line 8—8 of FIG. 7.

The coping sleeve may be fitted with mechanical means to lock it on the supra-gingival post against removal or shifting in the axial direction. FIGS. 5 and 6 show an exemplary bayonet mechanism, in which the anti-rotation longitudinal slots 17 on the post 15 are continued at one end in circumferential slots 27, and the radial projections 19 in the coping sleeve 16 are used to engage in the circumferential slots by rotating the coping sleeve 16 around the axis A—A of the supra-gingival post 15 after it has been installed on the post. FIGS. 7, 8 and 9 show a coping sleeve 30 in two coaxial parts 31, 32, the inner of which 32 can be rotated within the outer part 31 via a non-circular opening 33 in its top 34. The outer part 31 has the retention means 35 for holding a dental restoration rigidly fixed to it. The inner part 32 has internal size, shape and dimensions which match those of the supra-gingival post 15, including the projections 19 which cooperate with the grooves 17 and 27 on the post. When a restoration (not shown) has been formed on the coping sleeve 30, a hole is left in the top of the restoration through which a suitable wrench (e.g.: an Allen wrench) can be fitted into the hole 33 and the inner sleeve member 32 turned to engage the projections 19 in the circumferential slots 27. Thereafter, the hole in the restoration can be closed in a usual way, as with a bonding material.

Figure 10:
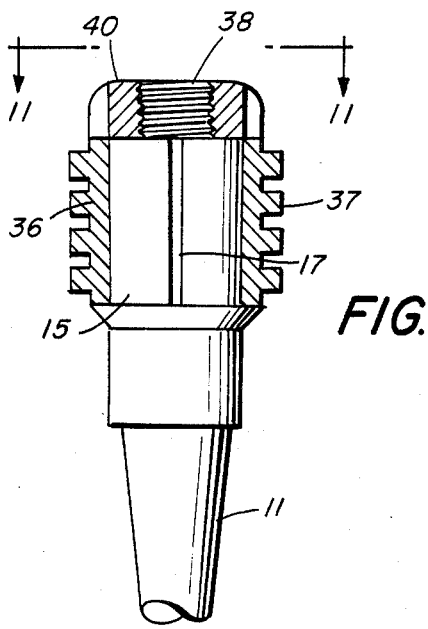
FIG. 10 is a longitudinal view of an endodontic post and a longitudinal sectional view of a coping sleeve, showing another embodiment of a locking mechanism for detachably fixing the coping sleeve on the post.
Figure 11:
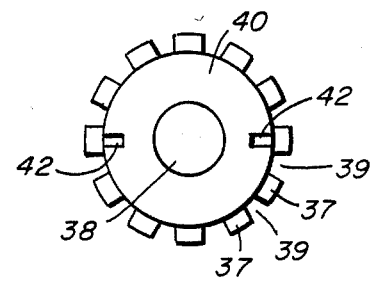
FIG. 11 is a view of the locking component of FIG. 10, taken on line 11—11.

FIGS. 10 and 11 show another locking mechanism. The supragingival post 15 has a head 38 of reduced diameter which is externally threaded. The coping sleeve 36 is a simple tube having retention means 37 on its outer surface. Otherwise it fits telescopically over the post 15 and engages the slots 17 for the rotation - inhibiting purpose already described.

Figure 11A:
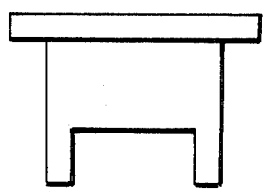
FIG. 11A shows a tool for operating the locking component.

An internally-threaded nut 40 fitted with a pair of radially outwardly extending slots 42 is threaded onto the head 38, to hold the coping sleeve 36 fixed on the post 15. As in the case of a bayonet lock, a restoration (not shown) that will be fixed on the coping sleeve 36 will have an aperture through it for access to the threaded head 38, so that the nut 40 can be screwed onto it. A spanner type screw driver, as shown in FIG. 11A, can be used.

As is indicated in FIG. 11, the retention means 37 need not be full annular extensions; indeed, it is preferred that the retention means 37 are block-like projections from the coping sleeve. The same is true of the coping sleeve 16 shown in FIG. 1. Nor is it necessary that block-like projections be used. A roughening of the external surface of the coping sleeve may be sufficient for many applications of the invention, as is shown at 44 on the outer surface of the coping sleeve 46 illustrated in FIG. 12.

Figure 12:
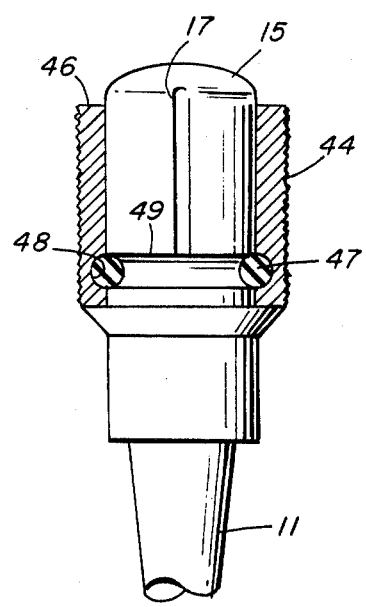
FIG. 12 shows another embodiment of a releasable retainer for holding the coping sleeve fixed on the post.

The locking mechanism shown in FIG. 12 consists simply of an O-ring 47 made of a resilient material (e.g.: rubber) and matching grooves 48, 49 of cylindrical, Vee, or other suitable cross sections in the coping sleeve and the supra-gingival post, respectively. The coping sleeve 46 is locked on the post 15 by pushing it firmly down over the O-ring in place on the post. As in FIG. 1, the coping sleeve 46 may be fitted with projections (not shown) for engaging in the anti-rotation groove or grooves 17 in the post 15.

Figure 13:
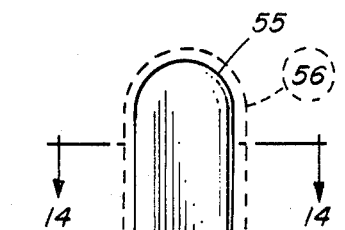
FIG. 13 illustrates a flattened endodontic post for use in restoring an anterior tooth.
Figure 14:
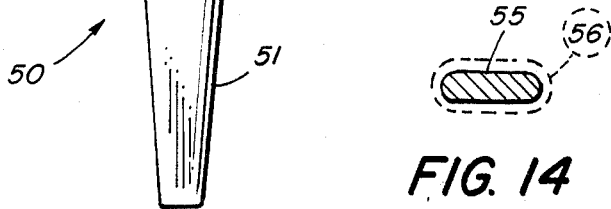
FIG. 14 is a section on line 14—14 of FIG. 13.

The endodontic post 50 shown in FIG. 13 is flattened to an ovoidal shape, for use in restoring an anterior tooth. The subgingival portion 51 is thinner than the width dimension shown in the drawing, and the supra-gingival post portion 55 is flattened as generally indicated in FIG. 14. A coping sleeve 56, indicated by dashed lines, has a corresponding shape. Owing to the ovoidal cross-sectional shape of the post 55 and coping sleeve 56, no additional anti-rotational measures are needed. Otherwise, the coping sleeve may have the same features as the coping sleeve 16, 30, 36 or 46.

The dowel pin 60 shown in FIGS. 15 and 16 has a supra-gingival post portion 65 which is an exact replica in size, shape and dimensions of the post 15 (or the post 55 if an anterior tooth is involved). The underlying retentive portion 61 is intended to be fixed in a rigid die material or the like (not shown) usually used in the dental laboratory to make a model from an impression for fabricating a dental restoration, and has means in the form of projections 62 for retaining the dowel pin in the die material. Desirably the retentive portion 61 has a non-circular cross section, shown for example in FIG. 16, so that the dowel pin will not rotate in the die material. As is indicated in FIG. 16, the projections 62 can be subdivided into blocks or the like by grooves 63 running lengthwise along the retentive portion 61.

Dowel pins according to FIG. 15 may be made of plastic material which may or may not be combustible, or of refractory materials such as aluminum oxide, or of metals such as brass.

Another dowel pin 70 intended for use to gain proximal and gingival access when shaping an individual abutment is shown in FIG. 17. This pin has a supra-gingival post portion 75 which again exactly replicates the size, shape and dimensions of the supra-gingival post portion 15, an anchoring portion 71 and a tapered removable pin portion 72 which has a non-round cross-section as shown in FIG. 18. According to known practice the model is made with two layers of rigid die material, a first layer 73 which replicates the impression and in which the anchoring portion 71 is fixed, and a second layer 74 in which the removable pin portion 72 is encased. Slits 76 are cut through the first layer on either side of the anchoring portion just outside the finishing lines for the intended restoration, and the removable pin portion 72 is pushed endwise from the narrow end to remove the unit consisting of the removable dowel pin 70 and the block of the first layer 73 of rigid die material that is fixed to the anchoring portion 71. A wax-up of a restoration can then be made on a coping sleeve 77 shown in dashed lines on the supragingival post portion 75. The surface 78 of the die material immediately surrounding the post portion 75 replicates the finishing line of the future restoration as reproduced by the impressions. A normal tooth 79 is indicated next to one of the slits 76.

A method of making a restoration according to the invention will now be described with the aid of FIGS. 19 and 15. In FIG. 19 a wax-up of a tooth 80 encasing a coping sleeve 77 is shown as though just removed from the supra-gingival post portion 75 of the removable dowel pin 70 of FIG. 17. The contours of the finishing line surface 78, and the matching contours in reverse 78' of the wax-up, are both shown. To make, for example, a gold crown, the wax-up 80 is placed on the supra-gingival post portion 65 of a dowel pin 60 of FIG. 15 which is made of a refractory material, and a sprue (not shown) is attached to the wax-up. Then, proceeding with a known lost-wax process, a precious or non-precious metal replica of the wax-up can be made on the refractory dowel pin 60. If the coping sleeve 77 is combustible, it will burn out with the wax, and the resulting crown will have a cavity which exactly replicates the internal size, shape and dimensions of the coping sleeve. If the coping sleeve 77 is non-combustible, it will be anchored firmly in the crown. In either case, the resulting crown can be put in place accurately and precisely merely by telescopically fitting it over the supra-gingival post that is fixed in the patient's mouth, from which the original impression was taken.

It is thus apparent that the invention can use existing laboratory procedures in a new, more precise, less labor intensive, and less time-consuming procedure to make dental restorations on a wide variety of sub-gingival supporting modalities. The procedure described with reference 15 and 19 is not limited to making of homogeneous crowns of metal. It is applicable also to crowns made of metallic substructures and porcelain or other outer superstructures, as well as homogeneous crowns made of porcelain, for example, using a high-fusing precious or non-precious metal coping sleeve.

The invention can also be used to fabricate a restoration at chairside. According to FIG. 20, a unitary package 90 provides a restoration kit including a coping sleeve such as the coping sleeve 16 (FIG. 1) together with a quantity of light-polymerizing or by other means catalyzed restorative material 91 in mastic form, in an envelope 92 made of a radiopaque material which is capable of preventing spontaneous polymerization of the restorative material. To use this package, the dentist opens the envelope at chairside, slips the coping sleeve 16 over a mating supra-gingival post 15 that has previously been installed in the patient's jawbone, and forms the restorative material into a rough shape of the restoration desired. The restorative material can be hardened with ultra-violet light, as is known, or other process. The package 90 can also be supplied with a pre-formed shell (not shown) which is in the shape of the desired restoration, in which case the dentist will put the shell over the restorative material 91 to establish its shape, before catalyzing the restoration on the coping sleeve 16. Preferably, the coping sleeve used for this application of the invention will be made of a non-metallic material which is colored in tones that will not adversely affect the cosmetics of the restoration. The coping sleeve can also have an external shape which is an anatomically correct miniature of the tooth to be formed on it, in particular for fashioning an anterior restoration, for example according to FIGS. 13 and 14.

A supra-gingival post 15 can also be supported as a cantilevered extension from an abutment coping 98, as is shown in FIG. 21. The coping 98 has an arm 99 extending laterally from it, on which the post 15 is fixed.

The foregoing description of the illustrated embodiments of the invention is intended to be exemplary, and not to limit the invention. Thus, for example, an osseointegrated implant of the kind described by Dr. L. G. Loos, "Journal of the California Dental Association," December 1984, pages 99–103 (FIGS. 1 and 2, page 100), can be used to support a supra-gingival post according to the invention.

I claim:

1. A replacement tooth comprising a supragingivally-extending post fixed in the patient's mouth, said post having prescribed external length and width dimensions, a precision fitting prefabricated sleeve having substantially the same internal width dimensions as said external dimensions of said post axially slidable on said post so as to be non-rotationally telescopically mated to said post, restorative material for forming said tooth surrounding said sleeve, and means on an external surface of said sleeve to retain said restorative material fixed relative to said sleeve.

2. A replacement tooth according to claim 1 including means to lock said sleeve on said post.

3. A replacement tooth according to claim 1 including means to restrain said sleeve against rotation around said post.

4. For forming a replacement tooth with precision fit, the combination of a support fixed in the patient's mouth, said support having a prefabricated supra-gingivally extending post, said post having prescribed external length and width dimensions, and a prefabricated coping sleeve having substantially the same internal width dimensions as said external width dimensions of said post axially slidable on said post for non-rotationally telescopically mating to said post, said sleeve having on an outer surface means to retain a dental restorative material.

5. A combination according to claim 4 including means to restrain said sleeve against rotation around said post.

6. A combination according to claim 4 including releasable means to lock said sleeve on said post, for removably fixing a tooth in place in a patient's mouth.

7. A combination according to claim 4 including a dental restorative material surrounding and fixed on said sleeve, said restorative material contoured in the shape of a replacement tooth.

8. A combination according to claim 4 including dental restorative material in a mastic state surrounding said sleeve, for forming a replacement tooth at chairside when said sleeve is fitted to said post.

9. A combination according to claim 8 including means to lock said sleeve against removal from said post.

10. A combination according to claim 8 in which said lock means is a snap-lock.

11. A combination according to claim 9 including means to provide access to said locking means for releasing said locking means.

12. A combination according to claim 4 in which said sleeve is made of a combustible material.

13. A combination according to claim 4 wherein said support is an endodontic post.

14. A combination according to claim 4 wherein said support is an implant.

15. A combination according to claim 4 wherein said support is an abutment.

16. A kit for use in forming a replacement tooth according to claim 4 comprising said sleeve and a charge of hardenable dental restorative material in a non-rigid state surrounding said sleeve, an air-tight envelope enclosing said sleeve and said charge, said envelope being made of a material which inhibits spontaneous hardening of said restorative material, whereby a dentist may form said replacement tooth at chairside by removing the contents from said envelope, placing said sleeve over said post, shaping said restorative material and then hardening the shaped restorative material.

17. A kit according to claim 16 including a shell which is contoured to the shape of a tooth, to form said non-rigid material into a desired shape.

18. A coping sleeve according to claim 4 comprising a first tubular part having on its outer surface said means to retain a dental restorative material, and a second part rotatably engaged within said first part, said second part having said internal width dimensions for telescopically mating to said post.

19. A coping sleeve according to claim 18 wherein said second part includes means to lock said coping sleeve against removal from said post.

20. A combination according to claim 4 including an externally threaded extension on said post, and an internally threaded lock member on said extension for retaining said sleeve on said post.

21. A dowel pin for constructing a die suitable for modeling or waxing up a dental crown, said pin having a supra-gingivally extending post on which to construct said dental crown, said post having prescribed external length and width dimensions, and a subgingival base that is embeddable in modeling stone, said base having means on its outer surface for retaining it fixed in said modeling stone in combination with a sleeve having substantially the same internal width dimensions as said external width dimensions of said post, said sleeve being axially slidable on said post so as to be non-rotationally telescopically matable to said post, and means on the outer surface of said sleeve to retain a dental restorative material.

22. A dowel pin according to claim 21 in which said base is followed by a tapered tail portion having smooth surfaces.

23. A dowel pin according to claim 21 made of a combustible material.

24. A dowel pin according to claim 21 made of a refractory material.

25. A matched set of articles for forming a replacement tooth with precision fit comprising a combination according to claim 4 and a dowel pin for constructing a die suitable for modeling or waxing up a dental crown intended to form said replacement tooth, said pin having a supra-gingivally extending modeling post on which to construct said dental crown, said modeling post having substantially the same external length and width dimensions as said post fixed in the patient's mouth, and a subgingival base that is embeddable in modeling stone, for modeling a crown that will fit precisely on said post fixed in the patient's mouth.

26. A method of fabricating a dental crown comprising the steps of fixing in the jawbone of a patient a supra-gingival post having prescribed external length and width dimensions and cross-sectional shape, telescopically fitting to said supra-gingival post a coping sleeve having internal length and width dimensions and cross-sectional shape which are substantially the same as said external length and width dimensions and cross-sectional shape, respectively, taking an impression of said supra-gingival post with said coping sleeve in place on it, together with the surrounding gingiva, slidably removing said impression including said coping sleeve from said post and surrounding gingiva, with said impression and said included coping sleeve fixing in a rigid modeling material a dowel pin having a modeling post with substantially the same external length and width dimensions and cross-sectional shape as said supra-gingival post, forming a model of said crown on said modeling post, removing said model from said modeling post, replicating said model and said internal dimensions and shape in a permanent dental restoration, and installing said restoration on said supra-gingival post.

27. A method according to claim 26 including the step of placing on said modeling post a coping sleeve made of a combustible material and having substantially the same internal length and width dimensions and cross-sectional shape as said supra-gingival post, waxing up said model of said crown on said combustible coping sleeve, and replicating said model in a permanent restoration by a lost-wax process during which said combustible coping sleeve is burned out along with the wax.

28. A method according to claim 26 including the step of placing on said modeling post a coping sleeve made of a non-combustible material and having substantially the same internal length and width dimensions and cross-sectional shape as said first-named coping sleeve, forming said model of said crown around said non-combustible coping sleeve on said modeling post, and replicating said model in a permanent dental restoration which includes said non-combustible coping sleeve.

29. A method of fabricating a dental restoration at chairside comprising the steps of fixing in the jawbone of a patient a supra-gingival post having prescribed external length and width dimensions and cross-sectional shape, telescopically fitting to said supra-gingival post a coping sleeve having substantially the same internal length and width dimensions and cross-sectional shape, covering said coping sleeve with a dental restorative material in a non-rigid state which is capable of being hardened by means available to dentists, forming a dental restoration on said coping sleeve with said restorative material, and hardening said restoration as it is formed at chairside from said restoration material.

30. A method according to claim 29 including maintaining a quantity of said restorative material in a non-rigid state in an airtight enclosure which includes said coping sleeve, opening said enclosure at chairside, and forming said restoration promptly after opening said enclosure.

* * * * *